July 24, 1973 J. L. TOMASOVIC, SR., ET AL Plant Pat. 3,372
CHRYSANTHEMUM PLANT
Filed April 6, 1971
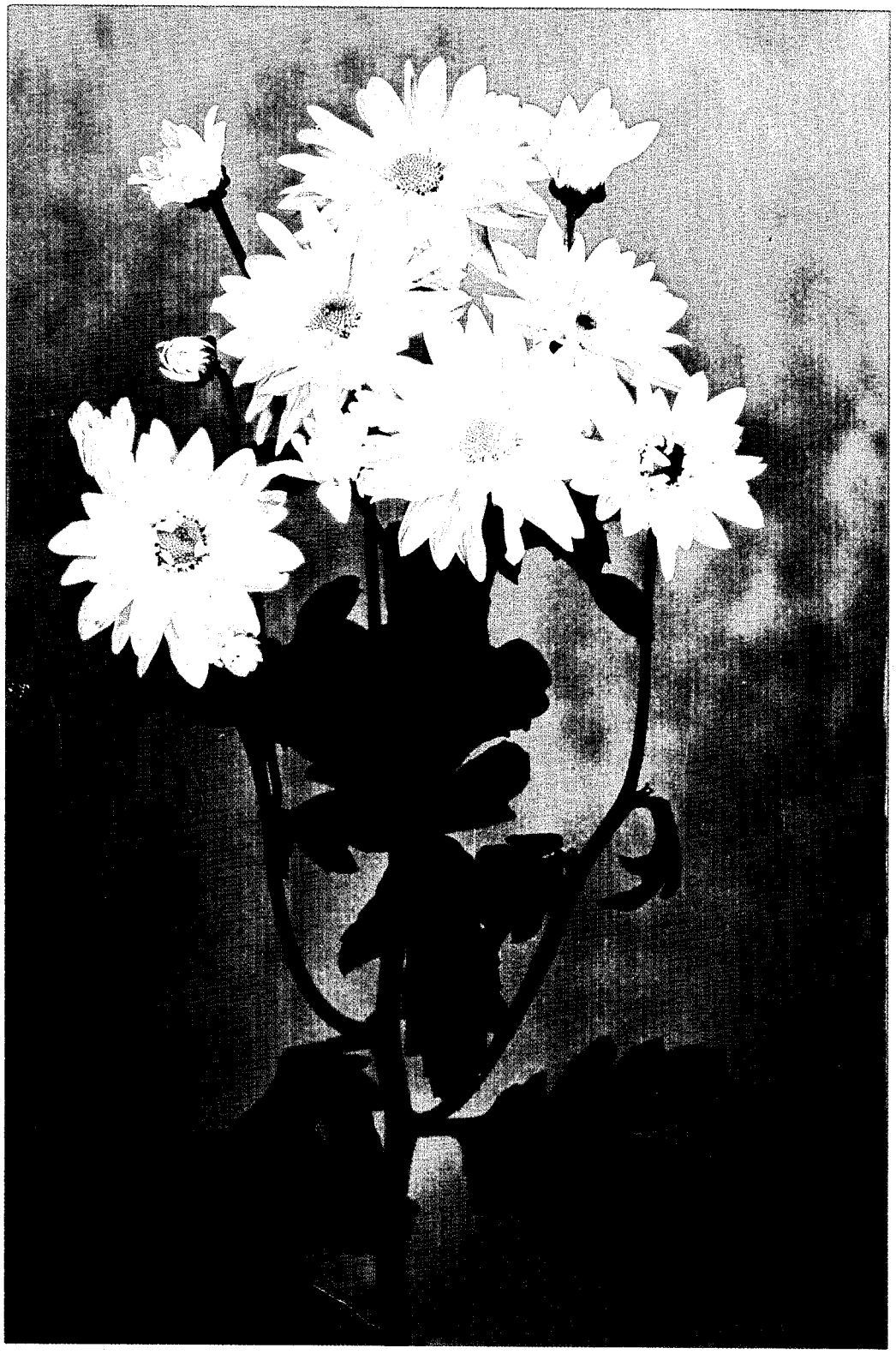

United States Patent Office

Plant Pat. 3,372
Patented July 24, 1973

3,372
CHRYSANTHEMUM PLANT

John L. Tomasovic, Sr., 1251 Meier Lane, St. Louis, Mo. 63131, and Walter H. Jessel, Jr., Doylestown, and William E. Duffett, Akron, Ohio; assignors to said John L. Tomasovic, Sr.

Filed Apr. 6, 1971, Ser. No. 131,705
Int. Cl. A01h *5/00*
U.S. Cl. Plt.—74 1 Claim

The present invention comprises a new and distinct variety of chrysanthemum plant which is a color sport of the white daisy cultivar Cononado, which is an unpatented but commercial variety of Yoder Brothers, Inc., Barberton, Ohio, assignee of the present invention.

The new variety is similar in many respects to Coronado, having the same characteristics of:

1. Flower shape
2. Flower size
3. Flowering response
4. Foliage size and shape

The new variety is distinguished from Coronado by the following characteristics:

1. A yellow flower color
2. Two to three inches less vigor

The new variety when discovered was growing with several plants of the parent variety Coronado, and was subsequently asexually reproduced by cuttings at Barberton, Ohio. The new variety has been found to retain its distinctive characteristics through successive propagations.

Our new variety when grown in the vicinity of Barberton, Ohio, has a response period of approximately 10 weeks. The response time and blooming period may vary significantly with varying environmental conditions such as temperature, day length, and light intensity.

Suggested flowering in the northern United States is from April through mid-November; in the southern United States, from mid-March through November, and coastal California, March through November.

The accompanying drawing illustrates the new variety, with the colors being as nearly true as possible with color illustrations of this type.

The following data is based on observations made of the new variety in a greenhouse in Barberton, Ohio. Color references are to the Munsel Color Book, 1963 edition, and comparisons have been made with the cultivar Coronado to show color differences.

*Botanical classifications:* Chrysanthemum morrifolium

Bloom:

*Size*—2¾".
*Fully expanded*—3¼".
*Borne*—Terminal cluster of 8–10 on elongated pedicels.
*Stems*—Elongated pedicels.
*Form*—Single.
*Permanence*—8–10 days.

| Color (Munsell) | Yellow Coronado | Coronado |
|---|---|---|
| Center of flower | Yellow, 6.25Y8/12 | Yellow, 6.25Y8/12. |
| Base of petals | Light yellow, 7.5Y8.5/8. | White, N9.5/. |
| Reverse of petals | Light yellow, 7.5Y9/6. | Do. |
| Tonality from a distance. | Lemon yellow | Do. |
| Discoloration | Light yellow | White. |

Petals:

*Texture.*—Smooth (ray florets); coarse (disc florets). Ray florets broadly keeled at base tapering to a blunt point; disc florets rudomentary with stigmas and styles protruding.
*Arrangement.*—Composite, whorled on a single receptacle.
*Persistence.*—Resist shatter.
*Fragrance.*—Typical chrysanthemum.

Reproductive organs:

*Stamen, anthers.*—200 more or less, depending on culture.
*Pollen.*—Abundant in cool periods to none during high temperature periods (functional sterility).
*Arrangement.*—Clustered in center of flower.
*Styles.*—Present in both ray and disc florets.
*Ovaries.*—At base of petals attached to receptacle.

Plant:

*Form.*—Herbaceous.
*Growth.*—Upright.

| | Yellow Coronado | Coronado |
|---|---|---|
| Height | Approximately 38"–44" on single stem crops given 2 to 4 long day weeks with 12–14 week crop time, depending on the season as recommended in the time-tables published by Yoder Bros., Inc. | Approximately 40"–46" on single stem crops given 2 to 4 long day weeks with 12–14 week crop time, depending on the season as recommended in the timetables published by Yoder Bros., Inc. |

*Spread.*—None when grown single stem; little when grown pinched.

Foliage:

*Top side.*—Green, 10GY¾.
*Size.*—6½"–7½" long, 3½"–4½" wide.
*Quantity.*—Numerous.
*Shape.*—Palmate.
*Texture.*—Coarse.
*Ribs and veins.*—Prominent.
*Edge.*—Indented.
*Serration.*—Slight.
*Underside.*—Light green, 7.5GY5/4.
*Stipules.*—Absent.

We claim:

1. A new and distinct variety of chrysanthemum characterized particularly as to its uniqueness compared to the white parent variety, Coronado, by its clear lemon-yellow color and its two to three inch less vigor.

No references cited.

ROBERT E. BAGWILL, Primary Examiner

UNITED STATES PATENT OFFICE

CERTIFICATE OF CORRECTION

Patent No. PP-3,372 Dated July 24, 1973

Inventor(s) JOHN L. TOMASOVIC, SR.; WALTER H. JESSEL, JR. and WILLIAM E. DUFFETT It is certified that error appears in the above-identified patent and that said Letters Patent are hereby corrected as shown below:

Column 1, line 11, "Cononado" should be --Coronado--.

Column 1, line 47, should read "Botanical classification: Chrysanthemum morifolium".

Column 2, line 4, "rudomentary" should be --rudimentary--.

Signed and sealed this 1st day of October 1974.

(SEAL)
Attest:

McCOY M. GIBSON JR.
Attesting Officer

C. MARSHALL DANN
Commissioner of Patents